United States Patent [19]

Gauri

[11] 4,020,070
[45] Apr. 26, 1977

[54] ALKYL-SUBSTITUTED 6-CHLORO-2-THIOURACILS

[75] Inventor: Kailash Kumar Gauri, Lentfoehrden, Germany

[73] Assignee: Robugen GmbH, Esslingen (Neckar), Germany

[22] Filed: Nov. 6, 1975

[21] Appl. No.: 629,535

Related U.S. Application Data

[63] Continuation-in-part of Ser. No. 369,232, June 12, 1973, abandoned.

[30] Foreign Application Priority Data

June 12, 1972 Germany .......................... 2228484

[52] U.S. Cl. .......................... 260/251 R; 424/251
[51] Int. Cl.² ........................................ C07D 239/10
[58] Field of Search .............................. 260/251 R

[56] References Cited

UNITED STATES PATENTS 3,330,640   7/1967   Luckenbaugh ................ 260/251 X

OTHER PUBLICATIONS

Gauri: Chemical Abstracts, vol. 73, 56051s (1970).

*Primary Examiner*—Lewis Gotts
*Assistant Examiner*—Dolph H. Torrence
*Attorney, Agent, or Firm*—Birch, Stewart, Kolasch & Birch

[57] ABSTRACT

A 2-thio-6-chlorouracil having the formula:

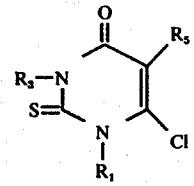

wherein $R_1$, $R_3$ and $R_5$ are the same or different and represent an alkyl, aryl or aralkyl group. $R_1$ can also be hydrogen or an alkenyl group. These compounds are useful as inhibitors of the enzyme, alcohol dehydrogenase.

11 Claims, No Drawings

ALKYL-SUBSTITUTED 6-CHLORO-2-THIOURACILS

This application is a continuation-in-part of copending application Ser. No. 369,232, filed on June 12, 1973, now abandoned.

This invention relates to substituted 2-thio-6-chlorouracils of the general formula

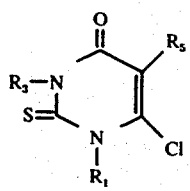

wherein $R_1$, $R_3$, and $R_5$, being identical or different, represent an alkyl, aryl, or aralkyl group, and $R_1$ can also represent a hydrogen atom or an alkenyl group.

The pharmaceutical industry is constantly striving to find new compounds which have useful pharmaceutical properties. The compounds of the present invention are novel and are particularly useful as inhibitors of alcohol dehydrogenase and are distinguished by an especially strong inhibitory activity in this regard. For instance, the compound of Example 1 below inhibits the activity of this enzyme to an extent of 49% at a concentration of $1.7 \times 10^{-3}$ M, while the compound of Example 2 below inhibits the activity of this enzyme to an extent of 22% at the same concentration. In contrast thereto, the conventional substance 1-allyl-3,5-diethyl-6-chlorouracil effects an inhibition of only 11% under identical experimental conditions.

Accordingly, one of the objects of the present invention is to provide novel organic compounds having useful pharmaceutical properties.

Another object of the invention is to provide alkyl-substituted 6-chloro-2-thiouracils and a process for preparing the same readily and efficiently.

A further object of the invention is to provide the said novel compounds having an especially strong inhibitory activity with respect to alcohol dehydrogenase.

These and other objects and advantages of the present invention will become apparent to those skilled in the art from a consideration of the following specification and claims.

The following examples are given as illustrative of preferred embodiments of the invention. These examples are not to be considered as limiting and are merely set forth in order to more clearly describe the invention.

EXAMPLE 1

3,5-Diethyl-6-chloro-2-thiouracil 10 g. of 3,5-diethyl-2-thiobarbituric acid is chlorinated, after the addition of a few drops of water, with excess phosphorus oxychloride (approximately 100 ml.) under heating for ¾ hour. The excess phosphorus oxychloride is distilled off, and the residue is poured on ice. The desired reaction product is crystallized during this step and melts, after recrystallization from aqueous ethanol, completely at 228° C. Yield: 70%

| Analysis: M.W. = 218.5 | | | | | |
|---|---|---|---|---|---|
| | C | H | N | Cl | S |
| Calculated: | 51.06 | 5.84 | 10.83 | 13.31 | 12.43 |
| Found: | 51.50 | 5.95 | 10.85 | 13.74 | 12.08 |

EXAMPLE 2

1-Allyl-3,5-diethyl-2-thio-6-chlorouracil 5 g. of 3,5-diethyl-2-thio-6-chlorouracil is heated under reflux in 15 ml. of allyl bromide and 10 ml. of acetone with the addition of about 4 g. of potassium carbonate for 24 hours. The thus-formed potassium chloride is filtered off and the residue fractioned under vacuum. The desired product is isolated as an oil by vacuum distillation. Yield: 90%

| Analysis: M.W. = 258.5 | | | | | |
|---|---|---|---|---|---|
| | C | H | N | Cl | S |
| Calculated: | 43.92 | 5.06 | 12.80 | 16.73 | 14.65 |
| Found: | 43.65 | 5.27 | 12.41 | 15.54 | 14.23 |

By proceeding in the same manner as described in the above examples it is possible to prepare 1-benzyl-3-ethyl-5-phenyl-2-thio-6-chlorouracil by alkylating 3-ethyl-5-phenyl-2-thio-6-chlorouracil with benzyl bromide and to prepare 1-allyl-3-ethyl-5-benzyl-2-thio-6-chlorouracil by alkylating 3-ethyl-5-benzyl-2-thio-6-chlorouracil with allyl bromide. Other compounds which can be prepared in accordance with this invention are 1-propyl-3,5-diethyl-6-chloro-2-thiouracil, 1-crotyl-3-methyl-5-propyl-6-chloro-2-thiouracil, 1-butyl-5-propyl-6-chloro-2-thiouracil and 1-benzyl-5-butyl-6-chloro-2-thiouracil. Each of these compounds possesses the useful pharmaceutical property discussed above.

In the above formula, $R_1$, $R_3$ and $R_5$ are alkyl, preferably lower alkyl of 1 to 4 carbon atoms including methyl, ethyl, propyl and butyl; aryl, preferably phenyl; or aralkyl, preferably phenylsubstituted lower alkyl groups such as benzyl, $R_1$, $R_3$ and $R_5$ may be the same or different. In addition, $R_1$ can be hydrogen or an alkenyl group of 1 to 4 carbon atoms such as allyl, crotyl or vinyl. The basic nucleus of the novel compounds of the invention is the 6-chloro-2-thiouracil group, and the designated alkyl substituents can be varied as indicated.

As noted above, the compounds of the present invention possess the property of strongly inhibiting the enzyme, alcohol dehydrogenase. The inhibition of alcohol dehydrogenase is a factor which parallels the chemotherapeutic action of a compound and, hence, this property is very significant in the pharmaceutical field; see in this connection Gauri et al, "Alkylated Pyrimidines: Relationship Between Structure and Fungistatic Activity", Biochemical Pharmacology, Vol. 23, pp. 1231-1234 (1974). Specifically, it is stated in the second paragraph on page 1232 of this paper that the in vitro test on the yeast-ADH "seems to be a well-suited criterion for the prediction and design of new fungistatic pyrimidines". Reference is also made in this regard to the paper by Gauri, "Pyrimidine Type Enzyme Inhibitors: I. Design of Active Pyrimidines of Virostatic Value", Chemotherapy, Vol. 15, No. 4, pp. 201-208 (1970).

Comparisons as to the inhibition of the activity of alcohol dehydrogenase (ADH) were carried out with the following compounds in accordance with the procedure as described by Buecher et al, *Klin, Wschr.*, 29, 615–616 (1951). In all cases, the following ingredients were used:

```
2.5 ml of phosphate buffer (pH 8.4) containing:
    Na₂P₂O₇ . 10H₂O           0.075M
    Semicarbazide . HCl       0.075M
    Glycine                   0.021M
0.1 ml NAD (0.5 × 10⁻² M)
0.1 ml ADH-Yeast (1:100)
0.1 ml ethanol
0.1 ml inhibitor (the test compounds as shown below)
```

The inhibitor concentration in these tests was $1.7 \times 10^{-3}$ molar. The test were conducted in a manner such that the active compounds showed an inhibition of approximately 50%. This provides a good basis for making comparisons with respect to the activity of different compounds. There are not absolute values per se for the activity of inhibitors, and comparisons of activity are relative.

Following the described procedure, the test results were as follows:

| Compound | AHD-inhibition |
| --- | --- |
| 3,5-diethyl-6-chloro-2-thiouracil | 49% |
| 1-allyl-3,5-diethyl-2-thio-6-chlorouracil | 22 |
| 1-allyl-3,5-diethyl-6-chlorouracil | 11 |
| 1-propyl-3,5-diethyl-6-chloro-2-thiouracil | 47 |
| 1-crotyl-3-methyl-5-propyl-6-chloro-2-thiouracil | 45 |
| 1-butyl-5-propyl-6-chloro-2-thiouracil | 28 |
| 1-benzyl-5-butyl-6-chloro-2-thiouracil | 20 |

From these results, it can be seen that the 2-thiouracil compounds of the present invention show a significantly greater alcohol dehydrogenase inhibition than the analogous prior art dioxo compounds such as 1-allyl-3,5-diethyl-6-chlorouracil.

The invention being thus described, it will be obvious that the same may be varied in many ways. Such variations are not to be regarded as a departure from the spirit and scope of the invention, and all such modifications are intended to be included within the scope of the following claims.

It is claimed:

1. A 2-thio-6-chlorouracil having the formula:

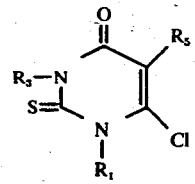

wherein $R_1$ is hydrogen, lower alkyl or alkenyl of 1 to 4 carbon atoms, phenyl or phenyl-substituted lower alkyl, and $R_3$ and $R_5$ are the same or different and are selected from the group consisting of lower alkyl of 1 to 4 carbon atoms.

2. A compound in accordance with claim 1, wherein $R_1$ is hydrogen, lower alkyl of 1 to 4 carbon atoms, phenyl, benzyl, allyl or crotyl.

3. The compound 3,5-diethyl-6-chloro-2-thiouracil.

4. The compound 1-allyl-3,5-diethyl-2-thio-6-chlorouracil.

5. The compound 1-benzyl-3-ethyl-5-phenyl-2-thio-6-chlorouracil.

6. The compound 1-allyl-3-ethyl-5-benzyl-2-thio-6-chlorouracil.

7. The compound 1-propyl-3,5-diethyl-6-chloro-2-thiouracil.

8. The compound 1-crotyl-3-methyl-5-propyl-6-chloro-2-thiouracil.

9. The compound 1-butyl-5-propyl-6-chloro-2-thiouracil.

10. The compound 1-benzyl-5-butyl-6-chloro-2-thiouracil.

11. A 2-thio-6-chlorouracil having the formula:

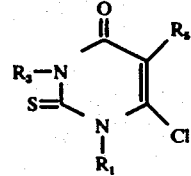

wherein $R_1$ is hydrogen, lower alkyl of 1 to 4 carbon atoms or crotyl, and $R_3$ and $R_5$ are the same or different and are selected from the group consisting of lower alkyl of 1 to 4 carbon atoms.

* * * * *